(12) United States Patent
Banavali et al.

(10) Patent No.: US 10,071,940 B2
(45) Date of Patent: *Sep. 11, 2018

(54) PROCESS FOR MAKING 2,3,3,3-TETRAFLUOROPROPENE AND/OR VINYLIDENE FLUORIDE

(71) Applicant: Honeywell International Inc., Morris Plains, NJ (US)

(72) Inventors: Rajiv Banavali, Morristown, NJ (US); Haridasan K. Nair, Williamsville, NY (US); Yian Zhai, Williamsville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/709,931

(22) Filed: Sep. 20, 2017

(65) Prior Publication Data

US 2018/0072642 A1    Mar. 15, 2018

Related U.S. Application Data

(63) Continuation of application No. 15/345,695, filed on Nov. 8, 2016, now Pat. No. 9,790,151.

(60) Provisional application No. 62/254,338, filed on Nov. 12, 2015.

(51) Int. Cl.
*C07C 17/361* (2006.01)

(52) U.S. Cl.
CPC ........... *C07C 17/361* (2013.01); *Y02P 20/582* (2015.11)

(58) Field of Classification Search
CPC ............................ C07C 17/361; C07C 17/383
See application file for complete search history.

(56) References Cited

U.S. PATENT DOCUMENTS

| | | |
|---|---|---|
| 2,427,116 A | 9/1947 | Barrick |
| 2,441,128 A | 5/1948 | Barrick et al. |
| 2,462,345 A | 2/1949 | Barrick |
| 2,848,504 A | 8/1958 | Dixon |
| 2,931,840 A | 4/1960 | Marquis |
| 2,982,786 A | 5/1961 | McCane |
| 3,996,299 A | 12/1976 | Fozzard |
| 3,996,301 A | 12/1976 | Fozzard |
| 4,086,407 A | 4/1978 | Fozzard |
| 5,026,499 A | 6/1991 | Merchant |
| 5,035,830 A | 7/1991 | Merchant |
| 6,624,337 B1 | 9/2003 | Manzer et al. |
| 8,058,486 B2 | 11/2011 | Merkel et al. |
| 8,084,653 B2 | 12/2011 | Tung et al. |
| 8,324,436 B2 | 12/2012 | Mukhopadhyay et al. |
| 8,618,340 B2 | 12/2013 | Kopkalli et al. |
| 8,975,454 B2 | 3/2015 | Merkel et al. |
| 9,061,957 B2 | 6/2015 | Mukhopadhyay et al. |
| 2008/0058562 A1 | 3/2008 | Petrov et al. |
| 2009/0099396 A1 | 4/2009 | Mukhopadhyay et al. |
| 2009/0186986 A1 | 7/2009 | Nomura et al. |
| 2011/0097529 A1 | 4/2011 | Durali et al. |
| 2014/0147480 A1 | 5/2014 | Lu et al. |
| 2014/0179887 A1 | 6/2014 | Lu et al. |

FOREIGN PATENT DOCUMENTS

| | | |
|---|---|---|
| WO | 200075092 A1 | 7/2007 |
| WO | 2009003085 A1 | 12/2008 |

OTHER PUBLICATIONS

Birchall et al. Cyclopropane Chemistry. Part III. Thermal Decomposition of Some Halogenopolyfluorocyclopropanes. Journal of the Chemical Society, Perkin Transactions 1: Organic and Bio-Organic Chemistry (1972-1999) (1973),(16), 1773-9. Language: English, Database: CAPLUS.

Placzek et al. The thermal isomerization of trifluoromethyl- and trifluoroethylcyclopropane. Journal of Physical Chemistry; vol. 69, Issue 7, 1965, pp. 2141-2145.

Sakaino, Structures and Chromotropic Properties of Imidazole Derivatives Produced from 3,6- Bis(4,5-diphenyl-2H-imidazol-2-ylidene)cyclohexa-I ,4-diene. J. Chem. Soc. Perkins Trans. I 1983.

Wlassics, I. 2p+2p cycloaddition kinetics of some fluoro olefins and fluoro vinyl ethers. Journal of Fluorine Chemistry 125 (2004) 1519-1528.

Hauptschein et al. The Thermal Dimerization of Perfluoropropene. Murray Hauptschein, Arnold H. Fainberg & Milton Braid. vol. 80. Feb. 20, 1958. 842-845.

Stoiljkovich, D. The Mechanism of the High-pressure Free Radical Polymerization of Ethylene. Journal of Polymer Science. Polymer Chemistry Edition. vol. 19, 741-747 (1981).

*Primary Examiner* — Jafar Parsa
(74) *Attorney, Agent, or Firm* — Bruce O. Bradford

(57) ABSTRACT

Disclosed is a process for the formation of a mixture of the compounds 2,3,3,3-tetrafluoropropene (HFO-1234yf) and vinylidene fluoride, comprising pyrolyzing 1,1,2-trifluoro-2-trifluoro-methyl-cyclobutane under conditions effective to produce a reaction product comprising HFO-1234yf and vinylidene fluoride in a 1234yf:vinylidene fluoride molar ratio of from about 0.5 to about 1.2.

21 Claims, No Drawings

PROCESS FOR MAKING 2,3,3,3-TETRAFLUOROPROPENE AND/OR VINYLIDENE FLUORIDE

CROSS-REFERENCE TO RELATED APPLICATIONS

This application is a continuation application from commonly owned, U.S. application Ser. No. 15/345,695, filed Nov. 8, 2016, now U.S. Pat. No. 9,790,151, the disclosure of which is hereby incorporated herein by reference. This application also claims domestic priority to commonly owned, U.S. Provisional Application Ser. No. 62/254,338, filed Nov. 12, 2015, the disclosure of which is hereby incorporated herein by reference.

BACKGROUND OF THE INVENTION

The hydrofluoro-olefin 2,3,3,3-tetrafluoropropene (HFO-1234yf, $CF_3CF=CH_2$) is a low global warming compound with zero ozone depletion potential which finds use as a refrigerant, a foam blowing agent, a monomer for polymers, and many other applications. A number of methods are known in the art for making HFO-1234yf. See, for example U.S. Pat. Nos. 8,975,454, 8,618,340, 8,058,486, and 9,061,957. See also, U.S. Patent Pub. Nos. 2009-0099396 and 2008-0058562.

Another route to HFO-1234yf is the hydrofluorination of 1,1,2,3-tetrachloro-propene (TCP), as disclosed in U.S. Pat. Nos. 8,084,653 and 8,324,436. PCT Publication No. WO 2009/003085 A1 describes the preparation of HFO-1234yf via the metathesis of hexafluoropropene (HFP) and ethylene. This process requires the use of an expensive metathesis catalyst in an organic solvent and thus not cost effective for commercial production.

These methods for making HFO-1234yf generally involve multiple steps, by-product formation, and have a low atom efficiency percentage. Atom efficiency percentage is calculated as follows:

(the molecular weight of the desired product) divided by (the molecular weight of the substances formed)×100.

The thermal dimerization of fluoro-olefins has been described in the literature. See, for example, U.S. Pat. Nos. 2,427,116; 2,441,128; 2,462,345; 2,848,504; 2,982,786; and 3,996,301. See also, J. Fluorine. Chem., 2004, 125, 1519; J. Chem. Soc., Perkin I, 1973, 1773; J. Chem. Soc., Perkin I, 1983, 1064.

U.S. Pat. No. 3,996,299 describes a process for the formation of a copolymer produced from vinylidene fluoride and 2,3,3,3-tetrafluoropropylene. This process involves the cyclodimerization of a perfluoroolefin, such as perfluoropropylene, with a terminal monoolefin, such as ethylene, to produce the cyclic compound 1,1,2-trifluoro-2-trifluoromethyl-cyclobutane (TFMCB). The cyclic compound such as TFMCB is then subjected to a thermal cracking operation to produce a mixture of acyclic fluorine-containing olefins, such as vinylidene fluoride and 2,3,3,3-tetrafluoro-propylene, which can be used as monomers and/or comonomers in polymerization reactions.

The '299 patent discloses the cyclodimerization reaction can occur over a very wide range of reaction conditions. For example, the patent indicates that the reaction temperature can be in the range of 200° to 600° C., preferably 300° to 400° C., and that the reaction time in the range of about 4 to about 1000 hours, preferably 10 to 100 hours. The '299 patent also indicates that the ratio of the monoolefin to the perfluoroolefin usually is in the range of 0.1:1 to about 100:1 preferably 1:1 to about 10:1.

The '299 patent discloses that the thermal cracking of the cyclic compound at temperatures in the range of 500° to 1000° C. and preferably in the range of 600° to 700° C. It is stated that the cracking reaction can be carried out continuously by passage through a heated reactor tube maintaining a contact time in the range of 0.01 to 10 seconds.

Applicants have come to recognize several problems and disadvantages associated with the formation of HFO-1234yf according to a process as described in the '299 patent. One such problem is that the '299 patent fails to recognize the potential problem in the cracking reaction associated with olefin oligomerization at high temperatures. Other problems are the presence of HFP and ethylene (the starting material) in the cracking products along with other side products, which are not mentioned in the '299 patent. Applicants have come to appreciate that these problems would be exacerbated under many of the dimerization reaction conditions specified in the '299 patent. The final reaction product is thus a complex mixture under the specified reaction conditions, especially with large excess of ethylene to HFP ratios. Another problem is that many of the permitted ratios of perfluoroolefin, such as HFP, to the monoolefin, such as ethylene, can produce undesirable reaction product results, including unwanted or detrimental by-products and/or poor conversions and/or selectivities. Similar disadvantages associated with unwanted or detrimental by-products and/or poor conversions and/or selectivities are possible within the range of reaction conditions for the cracking reaction.

At least in part as a result of the recognition of these problems with the prior art, applicants have developed new and greatly improved processes that provide significant and unexpected advantages in the production of HFO-1234yf and mixtures of HFO-1234yf and vinylidene fluoride (VDF).

SUMMARY OF THE INVENTION

One aspect of the present invention is directed to a process for making HFO-1234yf and/or vinylidene fluoride (VDF) comprising:
(a) reacting ethylene with hexafluoropropylene (HFP) in an ethylene:HFP mole ratio of greater than about 1:6 to less than about 1:1.2 for a contact time of not less than about 1 hour and not greater than about 100 hours and at an average reaction temperature of greater than about 250° C. and less than about 400° C. to produce 1,1,2-trifluoro-2-trifluoromethyl-cyclobutane (TFMCB) in a yield of at least about 40% and a selectivity of at least about 75%; and
(b) converting said 1,1,2-trifluoro-2-trifluoromethyl-cyclobutane (TFMCB) to VDF and/or HFO-1234yf, preferably by cracking, and more preferably in some embodiments by thermal cracking (hereinafter referred to as "pyrolysis"), said TFMCB in a reaction zone for a contact time of less than about 10 seconds and at an average temperature of less than about 850° C. to produce VDF and/or HFO-1234yf, preferably both VDF and HF-1234yf and even more preferably in a VDF:HFO-1234yf mole ratio of less than about 1.5:1 and not less than about 0.8:1.

Another aspect of the invention provides a process for forming VDF and/or HFO-1234yf comprising:

(a) providing a stream comprising 1,1,2-trifluoro-2-trifluoromethyl-cyclobutane (TFMCB); and
(b) cracking, and preferably pyrolyzing said 1,1,2-trifluoro-2-trifluoromethyl-cyclobutane (TFMCB) for a contact time of less than about 10 seconds and at an average temperature of less than about 850° C. to produce VDF and/or HFO-1234yf, preferably both VDF and HF-1234yf and even more preferably in a VDF:HFO-1234yf mole ratio of less than about 1.5:1 and not less than about 0.8:1.

One preferred embodiment of the pyrolysis reaction according to this aspect of the invention is depicted in Reaction Scheme I below:

Reaction Scheme I:

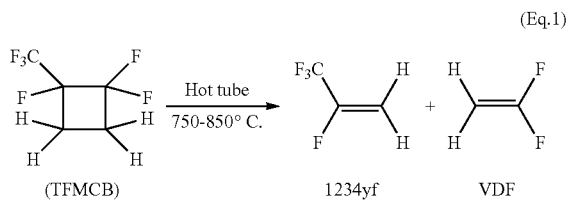

(Eq.1)

As described herein, one embodiment of this reaction is conducted by introducing into a reaction vessel, preferably into a heated tubular reaction vessel, a stream comprising, and preferably comprising in major proportion by weight, and even more preferably consisting essentially of, TFMCB. According to preferred embodiments the tubular reactor comprises aa stainless steel tube placed in a furnace maintained at elevated temperature and passing the TFMCB through the reactor, preferably in a continuous operation, at a contact time of less than about 10 seconds, more preferably less than about 5 seconds, to produce a reaction product stream comprising 1234yf and/or VDF, preferably both. Preferably, the embodiments include a quenching operation to quickly reduce the temperature of the reaction product to halt the pyrolysis reaction, such as for example, introducing the reaction product stream into a cylinder maintained at temperature much lower than the temperature of the heated reaction vessel. In some embodiments, no carrier gas (e.g., helium) is present in the reaction stream. The reaction temperatures preferably range from 500° C. to 1000° C., preferably from 750° C. to 850° C.

Although applicants do not intend to be bound by or to any particular theory of operation, it is believed that conducting the pyrolysis reaction in accordance with prior practice, as exemplified for example in the '299 patent, can result poor product yield and/or conversions as a result of, for example, over-cracking of the reactants, which in turn also has the potential disadvantage of resulting in low run times and/or high reactor fouling rates, potentially making such operations not commercially viable. Applicants have unexpectedly found that these and other disadvantages associated with prior operation can be avoided, and substantial and important improvements can be achieved, by operating the pyrolysis reaction within the process ranges described herein.

In certain embodiments, the pyrolysis provides a yield in the range of about 80% to about 90%, based on the amount of VDF and HFO-1234yf together, and preferably in a VDF:HFO-1234yf molar ratio of from about 1.5:1 to about 0.8:1. In certain embodiments, the pyrolysis provides a conversion rate of about 70%, based on the conversion of the starting materials.

In certain embodiments, the pyrolysis is conducted in a batch mode. In certain embodiments, the pyrolysis is conducted in a continuous mode.

In certain embodiments, the process further comprises a step of separating the mixture of the compounds HFO-1234yf and vinylidene fluoride, using conventional techniques.

The compound 1,1,2-trifluoro-2-trifluoromethylcyclobutane (TFMCB) is a known compound. TFMCB has a boiling point of 68° C. and was used as a component of a cleaning solvent composition in U.S. Pat. Nos. 5,026,499 and 5,035,830, which are incorporated herein by reference.

Methods for the synthesis of this compound are known. See for example, PCT Publication No. WO 2000/75092, which is incorporated herein by reference and which describes the codimerization of TFE and ethylene to give tetrafluorocyclobutane, and subsequent electrochemical fluorination give perfluorocyclobutanes. The compound 1,1,2-trifluoro-2-trifluoromethyl-cyclobutane (TFMCB) was also synthesized and fluorinated in this publication.

Another aspect of the invention provides improved methods for the preparation of TFMCB comprising: reacting ethylene with hexafluoropropylene (HFP) in an ethylene:HFP mole ratio of greater than about 1:6 to less than about 1:1.2 for a contact time of not less than about 1 hour and not greater than about 100 hours and at an average reaction temperature of greater than about 250° C. and less than about 400° C. to produce 1,1,2-trifluoro-2-trifluoromethyl-cyclobutane (TFMCB) in a yield of at least about 40% and a selectivity of at least about 75%. According to preferred embodiments of this aspect of the invention, the reaction comprises Reaction Scheme II as shown below:

Reaction Scheme II:

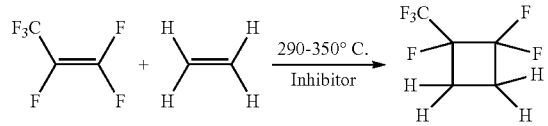

According to the preferred Reaction Scheme II, the synthesis of TFMCB, comprises the thermal dimerization of hexafluoropropene (HFP) and ethylene in the presence of a polymerization or oligomerization inhibitor. These starting materials are commercially available, and the resulting product is produced with high purity.

In certain embodiments, the reaction is conducted at a temperature in the range of from about 290° C. to 450° C., preferably from about 300° C. to 350° C.

In certain embodiments, the HFP and ethylene are present in the reactor at a molar ratio of from 1:2 to 1:10.

In certain embodiments, the HFP and ethylene are present in the reactor at a molar ratio of from 1:2 to 1:6.

As described above, the reaction mixture preferably includes one or more polymerization or oligomerization inhibitors. Suitable inhibitors include t-butyl catechol and similar compounds. Other well-known inhibitors include terpenes, such as limonene pinene and the like, and the quinone compounds, 1,4-naphtho-quinone, 2,5-di-tert-butyl-hydroquinone, hydroquinone, hydroquinone monomethyl ether, mono-tert-butyl hydroquinone, para-benzoquinone, toluhydroquinone, and trimethyl-hydroquinone; and the like.

In certain embodiments, the oligomerization inhibitor is present at from about 200 ppm to about 3% by weight. In certain embodiments, the oligomerization inhibitor is present at from about 500 ppm to 3000 ppm.

In certain embodiments, the thermal dimerization is conducted for a reaction time in the range of from about one to five hours.

In certain embodiments, at least a portion of unreacted starting materials contained in the reaction product are separated from the reaction product and recycled to the reactor and/or otherwise processed.

In certain embodiments, the reaction product stream contains at least about 92% on a molar basis of TFMCB. In certain embodiments, the product TFMCB is further purified by distillation to greater than about 99.8% purity.

Although applicants do not wish to be bound by or to any particular theory of operation, it is believed that operation of the dimerization reaction according to the preferred operating ranges disclosed herein avoid significant disadvantages that can be associated with conducting such operations according to the prior art, including for example the '299 patent. For example, applicants have unexpectedly found that product yield and/or product selectivity can be dramatically improved by operating the dimerization reaction within the operating parameters disclosed herein, and that operating outside certain of these parameters can cause a dramatic drop-off in conversion and/or yield, or can cause the production of detrimental byproducts. By way of further example, the present inventors have come to appreciate that the conditions which are needed to obtain the improved yield and selectivity of the present invention can result in unwanted and detrimental oligomerization of the reactants ethylene and/HFP. (see, J. Polymer Sci., 1981, 19, 741 and J. Am. Chem. Soc., 1958, 842). This problem was not recognized by the prior art, but applicants have found that serious disadvantages can be avoided by taking steps, as disclosed herein, to ensure that substantial oligomerization does not occur in the dimerization reaction.

For example, the present inventors have found that in certain embodiments severe oligomerization of ethylene and/or other unwanted side reactions can occur if polymerization inhibitor is not included in effective amounts, which in certain embodiments is at least about 200 ppm. In addition, the present inventors have discovered that conducting the reaction with the HFP:ethylene ratios described herein can produce the unexpected advantage of substantially eliminating or at least substantially reducing the formation of HFP or ethylene dimers or oligomers and/or accelerating the reaction of HFP-ethylene codimerization. The present inventors have also found that in certain embodiments and ethylene:HFP ratio greater than the preferred amounts disclosed herein can result in a surprising acceleration of the unwanted dimerization and/or oligomerization reaction(s).

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

One aspect of the present invention is directed to a process for the formation of a mixture of the compounds HFO-1234yf ($CF_3CF=CH_2$) and vinylidene fluoride ($F_2C=CH_2$) by the pyrolysis of a cyclobutane derivative made from ethylene and hexafluoropropene, namely, 1,1,2-trifluoro-2-tri-fluoromethyl-cyclobutane.

Unlike the process taught in U.S. Pat. Nos. 3,996,299 and 4,086,407, in a preferred embodiment no helium carrier gas is used, which reduces the cost and simplifies the purification of the reaction products.

The pyrolysis or cracking of 1,1,2-trifluoro-2-trifluormethyl-cyclobutane (TFMCB) is preferably conducted, preferably continuously, at an average temperature of from about 750° C. to about 800° C. in a suitable reactor (e.g., stainless steel or the like) to afford a mixture of both HFO-1234yf and VDF.

Typically, the thermal cracking of the neat cyclobutane compound in a hot tube reactor gave a mixture of 1234yf and VDF in excellent yield (atom efficiency percentage of about 80% to 90%) with a conversion of rate of about 70%. Approximately 3% to 5% of unreacted HFP and ethylene were observed in the product mixture. If desired, this mixture of compounds may be separated using conventional methods.

Since TFMCB is a liquid (bp 67° C.), it is conveniently added to the reactor via a heated mixer operated at about 100° C., which vaporizes the TFMCB. The tube reactor is first flushed with nitrogen and thereafter, neat liquid TFMCB is introduced to the heated zone at a predetermined flow rate, e.g., via a syringe pump or the like.

For the preparation of TFMCB in the examples, the compounds HFP and ethylene were mixed in a stainless cylinder reactor with a molar ratio of 1:2 to 1:10, preferably, 1:2 to 1:6, along with from 200 ppm to 3% of one or more oligomerization inhibitors, preferably 500 ppm to 3000 ppm, and heated to 250° to 550° C., preferably 290° to 400° C. for designated times (e.g., one to five hours).

Unreacted starting materials (HFP and/or ethylene) were recycled into a separate container and recycled. The final TFMCB product was decanted from the reactor with greater than 92% purity. Distillation through a column gives greater than 99.8% pure TFMCB.

The process can be carried out either continuously in a hot tube flow system or batch wise in a pressure vessel and the separation of products can be simultaneously or in separate steps. In general, the reaction can be performed sub-atmospherically, atmospherically, or super-atmospherically, e.g., within a pressure range of from 0.1 atm to 1000 atm.

It should be noted that during the pyrolysis of TFMCB in the examples, both HFP and ethylene were formed, each generated at about 3% to about 5%, between temperatures ranging from 500° C. to 900° C. This ratio did not change, even when changes were made to the pyrolysis conditions, including: temperature, contact time, and the presence or absence of carrying gases. This discovery was surprising in view of the teachings of the '299 and '407 patents discussed above, which disclosed no HFP and/or ethylene formation in the pyrolysis process.

EXAMPLES

The invention is further described by the following illustrative examples, which are not to be construed as limiting the scope of the invention.

Example 1—Pyrolysis of TFMCB

Pyrolysis of distilled TFMCB (495 g, 99.6%) was carried out in a heated stainless pipe reactor in a furnace (see Table II). The reactor was heated to and maintained at 800° C. for 30 minutes to equilibrate and was flushed with nitrogen. Liquid 1,1,2-trifluoro-2-(trifluoromethyl)-cyclobutane was introduced to the heated zone (100° C.) with a programmed syringe pump.

Once the flow of cyclobutane was started, the nitrogen flow was switched off and the pyrolysis was conducted in a continuous mode. The resulting pyrolysis products were collected in a cooled 1 gallon stainless steel cylinder. GC monitoring of products were done at the beginning and end of the reaction. Details are summarized in Table I below:

TABLE I

Scale Up Summary

| Item | Description |
|---|---|
| Reactor | Stainless steel (0.375" × 12"); Volume of heated zone = 10.85 cm$^3$ |
| Amount of cyclobutane used | 495.5 g (99.6% GC) |
| Temperature | 800° C. |
| Duration of pyrolysis | 7.83 h |
| Flow rate | 0.74 mL/min (liquid), 130 mL/min (vapor) (or 1.03 g/min) |
| Total products collected | 485.5 g |
| Mass balance | Mass loss = 495.5 − 485.5 = 10 g (2%) (Recovery = 98%) |
| Collection vessel/pressure | 1 gal SS cyl (~200-300 psi at RT); cooled by Liq N$_2$ while collecting. |
| Contact time (CT) | 5 sec [CT = Volume of heated zone cm$^3$/vapor flow rate in sccm] |
| Conversion | 70% |
| Yields | 1234yf (157.2 g, 81%); VDF (105.9 g, 97%) |

Conditions: temperature range ~700°-850° C.; Contact time ~1 to 60 sec range.

As shown in Table I, the laboratory scale reactor was made from stainless steel and had dimensions of 0.375 inches in diameter and a length of 12 inches, providing a heating zone of 10.85 cm$^3$. As indicated, the flow rate of the TFMCB provided a contact time of 5 seconds for the pyrolysis reaction. The collection vessel was also made from stainless steel and was cooled with liquid nitrogen during the collection of the reaction product mixture.

For production purposes, the reactor will be much larger, using suitable constructions materials for conducting the pyrolysis reaction on much greater amounts of TFMCB. Reaction temperatures may vary from those employed in the laboratory scale reactor. It is anticipated that the product composition of 1234yf/VDF to HFP/ethylene will not change, but the TFMCB conversion will be affected by changes in the operational temperatures. No carrier gas is expected to be used in a production plant. Finally, in production processing, the collection vessel will be much larger, and cooling will be provided by alternate means, such as cold water. In a production plant, it is anticipated that the product gas out of the reactor would be compressed into a pressurized storage vessel before distillation or further processing.

Comparative Examples 1A & 1B

1A. The purified TFMCB (3.0 g) from Example 3 was passed through a heated stainless tube reactor at 800° C. at 0.5 ml/min. The reaction tube had a diameter of 1.5 cm with a reaction zone length of 13.0 cm, which was filled with 6.8 g Inconel 625 mesh. The contact time with helium carrier gas of 66.7 ml/min was 14.1 sec, and 3.0 g of product gas was collected. GC analysis showed 3.8% ethylene, 48.7% VDF, 3.3% HFP, and 44.2% 1234yf.

1B. The reaction temperature was lowered to 750° C., 3.79 g of TFMCB was passed through the tube at 32.4 sec contact time. 3.78 g of product was recovered. GC analysis showed 3.8% ethylene, 48.9% VDF, 3.2% HFP, and 44.1% 1234yf.

Example 2

A number of reactions were carried out at various temperatures and contact times. Typically, the reactions were carried out by passing neat vaporized 1,1,2-trifluoro-2-(trifluoromethyl)-cyclobutane through a stainless tube/pipe reactor placed in a heated furnace. These results are shown below in Table II.

TABLE II

Pyrolysis of neat 1,1,2-trifluoro-2-(trifluoromethyl)cyclobutanes

| | | | cyclobut. Feed | Flow rate | | | Products -mixture Vol %* by GC | | | | | |
|---|---|---|---|---|---|---|---|---|---|---|---|---|
| Run # | 41923- | T (° C.) | Used (g) | Liq. Flow (mL/min) | Vap Flow (mL/min) | CT (sec) | Ethylene | VDF | HFP | 1234yf | Feed | Others |
| 11** | 32-4 | 700 | 31.80 | 0.20 | 35.41 | 18.4 | 5.01 | 60.17 | 2.29 | 30.18 | 0.05 | 2.3 |
| 12 | 33-1 | 750 | 4.78 | 0.76 | 133.67 | 4.9 | 3.72 | 48.74 | 3.23 | 42.12 | 1.68 | 0.51 |
| 13 | 33-2 | 800 | 5.23 | 1.25 | 219.38 | 3.0 | 3.69 | 46.48 | 3.09 | 40.54 | 5.76 | 0.44 |
| 14 | 33-3 | 750 | 3.93 | 0.94 | 164.85 | 3.9 | 3.63 | 47.27 | 3.18 | 41.52 | 3.83 | 0.57 |
| 15 | 33-4 | 750 | 5.45 | 1.20 | 211.03 | 3.1 | 3.68 | 45.93 | 3.15 | 40.88 | 5.9 | 0.46 |
| 16 | 33-5 | 750 | 4.32 | 0.78 | 135.91 | 4.8 | 3.69 | 47.58 | 3.29 | 43.02 | 0.02 | 2.4 |

TABLE II-continued

Pyrolysis of neat 1,1,2-trifluoro-2-(trifluoromethyl)cyclobutanes

| Run # | 41923- | T (° C.) | cyclobut. Feed Used (g) | Flow rate Liq. Flow (mL/min) | Flow rate Vap Flow (mL/min) | CT (sec) | Products -mixture Vol %* by GC | | | | | |
|---|---|---|---|---|---|---|---|---|---|---|---|---|
| | | | | | | | Ethylene | VDF | HFP | 1234yf | Feed | Others |
| 17 | 33-6 | 800 | 3.97 | 0.67 | 117.55 | 5.5 | 3.8 | 48.64 | 3.29 | 43 | 0.68 | 0.59 |
| 18 | 33-7 | 800 | 2.98 | 0.53 | 93.75 | 6.9 | 3.68 | 48.23 | 3.31 | 43.78 | 0.21 | 0.79 |

*volume % based on calibration by analytical dept. Tube Reactor: SS tube; ⅜" diameter, volume of heated zone 10.85 cm³.
**Done at 31.8 g scale and products collected 32 g in a cylinder.

As shown in Table II, the ratio of VDF to HFP was relatively constant and there remained about 2-5% of unreacted HFP and ethylene.

Example 3—Production of TFMCB

In a 1000-mL stainless steel cylinder was charged with 0.6 g t-butyl catechol, the cylinder is evacuated with nitrogen three times. Next, 52.0 g of HFP and 11.6 g of ethylene (mole ratio 1/1.19) were condensed into the cylinder. The cylinder was heated to 242° C. to 250° C. for 72 hours, and the inside pressure dropped from 600 psi to 500 psi at the end of reaction. Unreacted HFP and ethylene were recovered in a separate cylinder (39.6 g), and the product of 19.6 g was withdrawn from the reactor by vacuum. GC analysis showed 96.58% pure TFMCB.

Example 4—Production of TFMCB

A 2-L stainless cylinder was charged with 1.01 g of t-butyl catechol, and the cylinder is evacuated with nitrogen three times. Next, 50.0 g of HFP and 56.5 g of ethylene were condensed into the cylinder. The cylinder was heated to 320° C. to 329° C. for one hour, and the inside pressure dropped from 700 psi to 500 psi at the end of reaction. Unreacted HFP and ethylene were recovered in a separate cylinder (75.8 g), and the TFMCB product (29.4 g) was decanted from the reactor.

GC analysis showed 94.34% purity (46.2% yield based on HFP). Further distillation through a column gave 99.8% pure 1,1,2-trifluoro-2-trifluoromethyl-cyclobutane (TFMCB), $(CDCl_3)$ 2.62 ppm (m, 1H), 2.45 ppm (m, 2H), 2.24 ppm (m, 1H); $^{19}F$-NMR $(CDCl_3)$ −80.70 ppm (dt, J=9.3, 2.5 Hz, $CF_3$), −101.0 ppm (dm, J=212.9 Hz, 1F), −114.73 ppm (dtm, J=211.9, 16.2 Hz, 1F), −176.37 ppm (m, 1F).

Example 5—TFMCB Production

A 2-L stainless cylinder was charged with 1.10 g of t-butyl catechol, and the cylinder is evacuated with nitrogen three times. Next, a calculated amount of HFP and ethylene were condensed into the cylinder. The cylinder was heated to designated temperature for various time periods. The results were listed in Reaction Table III below.

Reaction Table III

| Entry | HFP/ Ethylene ratio | Temperature/ ° C. (time/h) | TFMCB Yield % (based on HFP) | Product selectivity % |
|---|---|---|---|---|
| 1 | 1.05/1.0 | 250 (72 h) | 15.4 | 96.6 |
| 2 | 1/1.19 | 242 (72 h) | 26.8 | 96.6 |
| 3 | 1/1.48 | 238 (120 h) | 30.5 | 95.0 |
| 4 | 1/1.97 | 256 (72 h) | 39.6 | 97.6 |
| 5 | 1/3.0 | 350 (19 h) | 89.6 | 77.4 |
| 6 | 1/3.35 | 375 (4 h) | 77 | 74.8 |
| 7 | 1/3.0 | 400 (1.2 h) | 110% yield (some oligomer of ethylene) | 58.4 |
| 8 | 1/0.9 | 400 (1 h) | 69 | 56.9 |
| 9 | 1/3.0 | 365 (3 h) | 90.8 | 84.8 |
| 10 | 1/3.0 | 370 (1.5 h) | 92.9 | 78.0 |
| 11 | 1/3.0 | 320-330 (5 h) | 97.9 | 91.4 |
| 12 | 1/6.17 | 320-331 (1 h) | 66.8 | 94.1 |

Example 6—TFMCB Production

A one-gallon stainless cylinder was charged with 60 mg of t-butyl catechol (200 ppm), and the cylinder is evacuated with nitrogen three times. Next, 140.7 g of HFP and 159.0 g of ethylene (mole ratio 1/6.05) were condensed into the cylinder. The cylinder was heated to 320° C. to 329° C. for one hour, and the inside pressure dropped from 800 psi to 600 psi at the end of reaction. Unreacted HFP and ethylene were recovered in a separate cylinder (174.5 g), and the product of 121.7 g was decanted from the reactor. GC analysis showed 78.10% of TFMCB, and 21.40% of side products from ethylene oligomers by GC and GCMS analysis.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A process for the formation of a mixture of the compounds 2,3,3,3-tetrafluoropropene (HFO-1234yf) and vinylidene fluoride, comprising pyrolyzing 1,1,2-trifluoro-2-trifluoro-methyl-cyclobutane to produce a reaction product comprising HFO-1234yf and vinylidene fluoride in a 1234yf:vinylidene fluoride molar ratio of from about 0.5 to about 1.2;
   wherein the pyrolysis is conducted at a temperature in the range of from about 750° C. to about 800° C. for a contact time of from about 2 seconds to about 25 seconds and at a pressure of about 1 atm.

2. The process of claim 1, wherein the pyrolysis is conducted in a stainless steel tube reactor and wherein the reaction is quenched by cooling as said reaction product comes out of the reactor.

3. The process of claim 1, wherein the pyrolysis provides a yield in the range of about 80% to about 90%.

4. The process of claim 1, wherein the pyrolysis provides a conversion rate of about 70%.

5. The process of claim 1, wherein the pyrolysis is conducted in a batch mode.

6. The process of claim 1, wherein the pyrolysis is conducted in a continuous mode.

7. The process of claim 1, further comprising the step of separating the mixture of the compounds 1234yf and vinylidene fluoride.

8. A process for the formation of a mixture of the compounds 2,3,3,3-tetrafluoropropene (HFO-1234yf) and vinylidene fluoride, comprising pyrolyzing 1,1,2-trifluoro-2-trifluoro-methyl-cyclobutane to produce a reaction product comprising HFO-1234yf and vinylidene fluoride in a 1234yf:vinylidene fluoride molar ratio of from about 0.5 to about 1.2;
   wherein the pyrolysis is conducted at a temperature in the range of from about 750° C. to about 800° C. for a contact time of from about 2 seconds to about 25 seconds and at a pressure of about 1 atm; and
   further comprising the step of forming the compound 1,1,2-trifluoro-2-trifluoromethyl-cyclobutane (TFMCB) by the thermal dimerization a mixture of hexafluoro-propene (HFP) and a stoichiometric excess of ethylene, in the presence of a polymerization or oligomerization inhibitor.

9. The process of claim 8, wherein the HFP and ethylene were mixed in a reactor at a molar ratio of from 1:1 to 1:10.

10. The process of claim 8, wherein the HFP and ethylene were mixed in a reactor at a molar ratio of from 1:1 to 1:6.

11. The process of claim 8, wherein the inhibitor is present at from about 200 ppm to about 3% by weight.

12. The process of claim 8, wherein the inhibitor is present at from about 500 ppm to 5000 ppm.

13. The process of claim 8, wherein the inhibitor is selected from the group consisting of catechol and catechol derivatives, terpenes, quinones and combinations of two or more thereof.

14. The process of claim 8 wherein said inhibitor is selected from the group consisting of t-butyl catechol, limonene, pinene, 1,4-naphtho-quinone, 2,5-di-tert-butyl-hydroquinone, hydroquinone, hydroquinone monomethyl ether, mono-tert-butyl hydroquinone, para-benzoquinone, toluhydroquinone, trimethyl-hydroquinone and combinations of any two or more thereof.

15. The process of claim 8, wherein the thermal dimerization is conducted at a temperature in the range of from about 250° C. to 450° C.

16. The process of claim 8, wherein the thermal dimerization is conducted at a temperature in the range of from about 300° to 350° C.

17. The process of claim 14, wherein the thermal dimerization is conducted for a reaction time in the range of from about one to five hours.

18. The process of claim 15, wherein the thermal dimerization is conducted for a reaction time in the range of from about one to five hours.

19. The process of claim 8, wherein any unreacted starting materials are recycled into a separate container.

20. The process of claim 8, wherein the product TFMCB is decanted from the reactor at greater than 92% purity.

21. The process of claim 8, wherein the product TFMCB is purified by distillation at greater than 99.8% purity.

* * * * *